United States Patent [19]  
Friebe et al.

[11] Patent Number: 4,931,462
[45] Date of Patent: Jun. 5, 1990

[54] HETEROCYCLIC SUBSTITUTED ALKYLSULPHONAMIDES PHARMACEUTICAL COMPOSITIONS CONTAINING THEM, AND ARTERIAL DISEASE TREATMENT THEREWITH

[75] Inventors: Walter-Gunar Friebe; Erhard Reinholz, both of Mannheim; Liesel Doerge, Lampertheim; Karlheinz Stegmeier, Heppenheim, all of Fed. Rep. of Germany

[73] Assignee: Boehringer Mannheim GmbH, Mannheim, Fed. Rep. of Germany

[21] Appl. No.: 287,888

[22] Filed: Dec. 21, 1988

[30] Foreign Application Priority Data

Dec. 24, 1987 [DE] Fed. Rep. of Germany ....... 3744141
Feb. 15, 1988 [DE] Fed. Rep. of Germany ....... 3804636

[51] Int. Cl.$^5$ ................. C07D 209/34; C07D 307/82; A61K 31/395; A61K 31/34
[52] U.S. Cl. ..................... 514/419; 514/469; 548/492; 549/57
[58] Field of Search .......... 549/57; 548/492; 514/419, 469

[56] References Cited

FOREIGN PATENT DOCUMENTS 1463665 2/1977 United Kingdom .
1463670 2/1977 United Kingdom .
1465651 2/1977 United Kingdom .

Primary Examiner—David B. Springer
Attorney, Agent, or Firm—Felfe & Lynch

[57] ABSTRACT

New Sulphonamides of the formula:

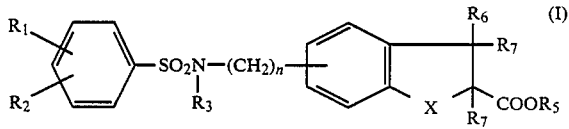

wherein $R_1$ and $R_2$, which can be the same or different, are hydrogen or halogen atoms, $C_1$–$C_6$-alkyl, $C_1$–$C_6$-alkoxy, $C_1$–$C_6$-alkylthio, $C_1$–$C_6$-alkylsulphinyl, $C_1$–$C_6$-alkylsulphonyl or trifluoromethyl radicals or hydroxyl or cyano groups, $R_3$ and $R_8$, which can be the same or different, are hydrogen atoms, $C_1$–$C_6$-alkyl, benzyl or $C_1$–$C_6$-alkanoyl radicals, $R_4$ and $R_5$, which can be the same or different, are hydrogen atoms or $C_1$–$C_6$-alkyl radicals, $R_6$ and $R_7$ are both hydrogen atoms or together form a valency bind, X is an oxygen or sulphur atom or an =NOH or =$NR_8$ group and n is a whole number of from 1 to 4; and the physiologically acceptable salts thereof with inorganic and organic bases. These compounds are useful for example in the treatment of asthma or cardiovascular disease, thrombosis prevention and treatment, and to combat broncoconstriction.

21 Claims, No Drawings

HETEROCYCLIC SUBSTITUTED ALKYLSULPHONAMIDES PHARMACEUTICAL COMPOSITIONS CONTAINING THEM, AND ARTERIAL DISEASE TREATMENT THEREWITH

The present invention is concerned with new heterocyclic substituted alkylsulphonamides, processes for the preparation thereof and pharmaceutical compositions containing them.

The new sulphonamides according to the present invention are compounds of the general formula:

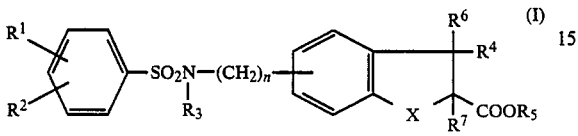

wherein $R_1$ and $R_2$, which can be the same or different, are hydrogen or halogen atoms, $C_1-C_6$-alkyl, $C_1-C_6$-alkoxy, $C_1-C_6$-alkylthio, $C_1-C_6$-alkylsulphinyl, $C_1-C_6$-alkylsulphonyl or trifluoromethyl radicals or hydroxyl or cyano groups, $R_3$ and $R_8$, which can be the same or different, are hydrogen atoms or $C_1-C_6$-alkyl, benzyl or $C_1-C_6$-alkanoyl radicals, $R_4$ and $R_5$, which can be the same or different, are hydrogen atoms or $C_1-C_6$-alkyl radicals, $R_6$ and $R_7$ are both hydrogen atoms or together represent a valency bond, X is an oxygen or sulphur atom or an $=NOH$ or $=NR_8$ group and n is a whole number of from 1 to 4, and the physiologically acceptable salts thereof with inorganic or organic bases.

If the compounds of general formula (I) contain an asymmetric carbon atom, the optically-active compounds and the racemic mixtures are also the subject of the present invention.

The new compounds of general formula (I) possess valuable pharmacological properties. In particular, they show an excellent antagonistic action towards thromboxane $A_2$, as well as against prostaglandin endoperoxides. They inhibit the aggregation of blood platelets and prevent the constriction of the smooth musculature, as well as bronchoconstriction. Furthermore, they are valuable medicaments for the treatment of pathological changes of the kidney function.

These properties make them valuable medicaments for the treatment of, for example, cardiovascular diseases and of asthma and for the prophylaxis of the shocked lung. Furthermore, they can be used in the case of organ transplants and for kidney dialysis and are suitable recidivitly to prevent gastric ulcers. An especial importance is the possibility of favourably influencing or preventing thrombotic processes. They can be used for the treatment of peripheral arterial occlusive diseases and can be used, for example, against cerebral and ischaemic states.

When $R_1$, $R_2$, $R_3$, $R_4$, $R_5$ or $R_8$ stand for alkyl, alkoxy, alkylthio, alkylsulphinyl, alkylsulphonyl or alkanoyl radicals, then the alkyl moiety thereof can be straight-chained or branched. The methyl, ethyl, propyl, isopropyl, butyl, sec.-butyl, tert.-butyl, pentyl and hexyl radicals are preferred.

The halogen atoms can be fluorine, chlorine or bromine.

Preferred compounds according to the present invention are compounds of general formula (I) in which $R_1$, $R_3$ and $R_8$ are hydrogen atoms, $R_2$ is a hydrogen, bromine or chlorine atom or a methyl or methoxy radical, $R_4$ is a hydrogen atom or a methyl radical, $R_5$ is a hydrogen atom or an ethyl radical, $R_6$ and $R_7$ together form a valency bond, X is an oxygen or sulphur atom or an $=NR_8$ group and n is 1 or 2 and the sulphonamido radical is in the 5-position of the heterocyclic moiety.

The present invention also provides a process for the preparation of the compounds of general formula (I) wherein, in known manner, either (a) a compound of the general formula:

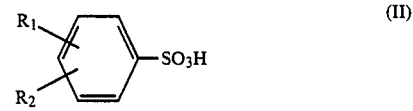

in which $R_1$ and $R_2$ have the above-given meanings, or a reactive derivative thereof, is reacted with a compound of the general formula:

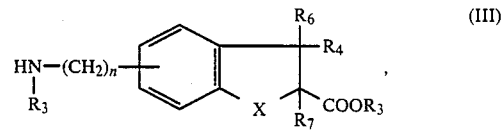

in which $R_3$, $R_4$, $R_5$, $R_6$, $R_7$, X and n have the above-given meanings; or (b) a compound of the general formula:

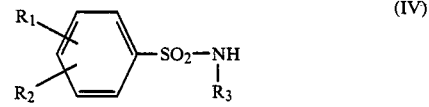

in which $R_1$, $R_2$ and $R_3$ have the above-given meanings, is reacted with a compound of the general formula:

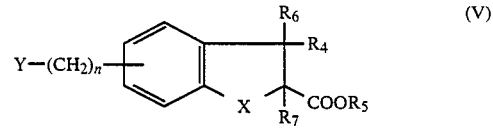

in which $R_4$, $R_5$, $R_6$, $R_7$, X and n have the above-given meanings and Y is a reactive residue; or (c) when X is an $=NH$ group and $R_6$ and $R_7$ together form a valency bond, a compound of the general formula:

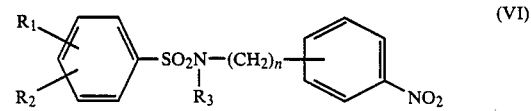

in which $R_1$, $R_2$, $R_3$ and n have the above-given meanings, is reduced according to a combined Japp-Klingemann/Fischer indole synthesis, the resultant amino group is converted in known manner into a diazonium group, the diazonium group is reacted with a 2-methylacetoacetic acid ester and the resultant hydrazone is cyclised to give an indole; and subsequently, if desired, a radical $R_3$, $R_5$ or $R_8$ is converted into a different radical $R_3$, $R_5$ or $R_8$ as defined above; a valency bond formed by $R_6$ and $R_7$ together is removed by hydrogenolysis; an alkylthio radical $R_1$ or $R_2$ is converted by oxidation into an alkylsulphinyl or alkylsulphonyl radical; an alkoxy radical $R_1$ or $R_2$ is converted into a hydroxyl group or a hydroxyl group $R_1$ or $R_2$ is converted into an alkoxy radical; and the compounds obtained of general formula (I) are, if desired, converted into physiologically acceptable salts by neutralisation with non-toxic bases.

The reaction of a compound of general formula (II) with a compound of general formula (III) is advantageously carried out in a solvent or solvent mixture, for example dichloromethane, diethyl ether, tetrahydrofuran, dioxan or benzene, optionally in the presence of an acid-binding agent, for example sodium carbonate, triethylamine or pyridine, in which case the two latter can also serve simultaneously as solvent, in the presence of an agent activating the acid or removing water, for example thionyl chloride or phosphorus pentachloride, but preferably with a reactive derivative of a compound of general formula (II), for example an anhydride or halide, preferably at a temperature of from 0° to 100° C., for example at a temperature from ambient temperature to 50° C.

The reactive residue Y is preferably a halogen atom, for example a chlorine or bromine atom, or an aliphatic or aromatic sulphonyloxy radical, for example a methanesulphonyloxy or p-toluenesulphonyloxy radical.

The reaction of a compound of general formula (IV) with a compound of general formula (V) is advantageously carried out in a solvent, for example acetone, diethyl ether, benzene, toluene or dimethylformamide, at a temperature of from −30° to +100° C. and preferably at ambient temperature in the presence of a base, for example potassium carbonate or sodium hydride, or also in an alcohol in the presence of an alkali metal alcoholate.

Most of the compounds of general formula (III) are new and can be synthesised from known precursors by processes known from the literature. Thus, for example, halomethyl derivatives of benzofuran-, benzothiopheneor indole-2-carboxylic acid are reacted with cyanides to give the corresponding cyanomethyl compounds which are subsequently reduced to the aminoethyl derivatives. Compounds of general formula (III) in which n is 1 are obtained directly from the halomethyl derivatives by reaction with $R_3NH_2$.

The halomethyl derivatives of general formula (V) (n=1, Y=Cl) are obtained by the chloromethylation of the corresponding heterocyclic compounds.

The conversion of compounds of general formula (I) into other compounds of general formula (I) can take place by conventional methods.

If, for example, $R_3$ or $R_8$ stands for a hydrogen atom, this can be substituted by an alkyl radical by reaction with an alkyl halide, alkyl sulphonate or alkyl sulphate or can be substituted by an alkanoyl radical by reaction with a carboxylic acid or an activated carboxylic acid derivative, for example an anhydride, halide or ester.

An alkanoyl radical $R_3$ or $R_8$ can be replaced by a hydrogen atom by acid or alkaline hydrolysis or alcoholysis.

The conversion of a radical $R_5$ can take place, for example, by saponification, esterification or transesterification.

The hydrogenolysis of a valency bond formed by $R_6$ and $R_7$ together is advantageously carried out in a solvent, for example, water, aqueous ethanol, methanol, acetic acid, ethyl acetate, tetrahydrofuran or dimethylformamide, with hydrogen or hydrazine in the presence of a hydrogenation catalyst, for example Raney nickel, platinum or palladium-charcoal.

The oxidation of an alkylthio radical $R_1$ or $R_2$ is preferably carried out in a solvent or solvent mixture, for example water, alcohol, aqueous pyridine, acetone, acetic acid, dilute sulphuric acid or trifluoroacetic acid, at a temperature of from −80° to +100° C.

For the production of an alkylsulphinyl radical, the oxidation is advantageously carried out with one equivalent of the oxidation agent used, for example with hydrogen peroxide in glacial acetic acid, trifluoroacetic acid or formic acid, at 0° to 20° C. or in acetone at 0° to 60° C., with a per acids, for example performic acid, in glacial acetic acid or trifluoroacetic acid, at 0° to 50° C., or with m-chloroperbenzoic acid in dichloromethane or chloroform at −20° to +60° C., with sodium metaperiodate in aqueous methanol or ethanol at −15° C. to +25° C., with bromine in glacial acetic acid or aqueous acetic acid, with N-bromosuccinimide in ethanol, with tert.-butyl hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. or with sulphuryl chloride in dichloromethane at −70° C., the thioether-chlorine complex thereby obtained is advantageously hydrolysed with aqueous ethanol.

For the preparation of an alkylsulphonyl radical, the oxidation is advantageously carried out with two or more equivalents of the oxidation agent used, for example with the above-mentioned reagents, if desired at a higher temperature of up to 100° C.

The conversion of an alkoxy radical $R_1$ or $R_2$ into a hydroxyl group is carried out either in the presence of an acid, for example hydrobromic acid or hydroiodic acid, of a solution of hydrogen bromide in glacial acetic acid or hydrogen chloride in pyridine or in the presence of a Lewis acid, for example aluminium chloride, boron trichloride or boron tribromide, in a solvent, for example dichloromethane, at a temperature of from −80° to +100° C.

The alkylation of a hydroxyl group $R_1$ or $R_2$ is preferably carried out in a solvent, for example, acetone, alcohol, diethyl ether, benzene, toluene or dimethylformamide, at a temperature of from −30° to +100° C. and preferably at ambient temperature in the presence of a base, for example potassium carbonate, sodium hydride or an alkali metal alcoholate, by reaction with an alkylation agent, for example an alkyl halide, alkyl sulphate or alkyl sulphonate.

For the preparation of salts with physiologically acceptable organic or inorganic bases, for example sodium hydroxide, potassium hydroxide, calcium hydroxide, ammonium hydroxide, methylglucamine, morpholine, triethylamine or ethanolamine, the compounds of general formula (I), in which at least one of the symbols $R_3$ or $R_5$ is a hydrogen atom, are reacted with the appropriate bases. Mixtures of acidic compounds can also be reacted with an appropriate alkali metal carbonate or hydrogen carbonate.

For the preparation of pharmaceutical compositions, the compounds of general formula (I) are mixed in known manner with appropriate pharmaceutical carrier substances, aroma, flavouring and colouring materials and formed, for example, into tablets or dragees and, with the addition of appropriate adjuvants, suspended or dissolved in water or an oil, for example olive oil.

The compounds of general formula (I) can be administered orally or parenterally in liquid or solid form. As injection medium it is preferred to use water which contains the stabilising agents, solubilising agents and/or buffers usual in the case of injection solutions. Such additives include, for example, tartrate and borate buffers, ethanol, dimethyl sulphoxide, complex formers (such as ethylenediamine-tetraacetic acid), high molecular weight polymers (such as liquid polyethylene oxide) for viscosity regulation or polyethylene derivatives of sorbit anhydrides. Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The dosage administered depends upon the age, state of health and weight of the recipient, the extent of the disease, the nature of further treatments possibly carried out simultaneously, the frequency of the treatments and the nature of the desired action. The daily dosage of the active compound is usually from 0.1 to 50 mg./kg. body weight. Normally, 0.5 to 40 and preferably 1.0 to 20 mg./kg. in one or more administrations per day are effective for obtaining the desired results.

Apart from the compounds of general formula (I) mentioned in the following Examples, as well as the salts thereof, the following compounds are also especially preferred according to the present invention:

5-[2-(3-trifluoromethylbenzensulphonamido)-ethyl]-benzo-[b]-furan-2-carboxylic acid 5-[2-(4-cyanobenzenesulphonamido)-ethyl]-benzo[b]furan-2-carboxylic acid 5-[2-(4-methylthiobenzenesulphonamido)-ethyl]-benzo[b]-furan-2-carboxylic acid 5-[2-(4-methylsulphinylbenzenesulphonamido)-ethyl]-benzo[b]furan-2-carboxylic acid 5-[2-(4-methylsulphonylbenzenesulphonamido)-ethyl]-benzo[b]furan-2-carboxylic acid 5-[2-(4-hydroxybenzenesulphonamido)-ethyl]-benzo[b]-furan-2-carboxylic acid 5-[(2,4-dimethylbenzenesulphonamido)-ethyl]-benzo[b]-furan-2-carboxylic acid 5-[2-(N-benzyl-4-chlorobenzenesulphonamido)-ethyl]-benzo[b]furan-2-carboxylic acid 5-[2-(4-N-acetyl-4-chlorobenzenesulphonamido)-ethyl]-benzo[b]furan-2-carboxylic acid 5-[3-(4-chlorobenzenesulphonamido)-propyl]-benzo[b]-furan-2-carboxylic acid 5-[4-(4-chlorobenzenesulphonamido)-butyl]-benzo[b]-furan-2-carboxylic acid 5-[2-(4-chlorobenzenesulphonamido)-ethyl]-N-acetylindole-2-carboxylic acid 5-[2-(4-chlorobenzenesulphonamido)-ethyl]-N-benzoylindole-2-carboxylic acid The following Examples are given for the purpose of illustrating the present invention:

EXAMPLE 1.

Ethyl 5-[2-(4-chlorobenzenesulphonamido)-ethyl]-benzo[b]furan-2-carboxylate.

A suspension of 8.1 g. (30 mMole) ethyl 5-(2-aminoethyl)-benzo[b]furan-2-carboxylate hydrochloride in 100 ml. dichloromethane is mixed with 10.0 g. (100 mMole) triethylamine, cooled to 5° C. and a solution of 8.4 g. (40 mMole) 4-chlorobenzenesulphochloride added dropwise thereto. The reaction mixture is stirred for 4 hours at at ambient temperature, evaporated, the residue taken up in ethyl acetate, washed neutral, evaporated and chromatographed on silica gel. Elution with dichloromethane gives 5.5 g. of the title compound; yield 45% of theory; m.p. 123°-125° C.

The starting material can be prepared as follows: By the reaction of ethyl 5-chloromethylbenzo[b]furan-2-carboxylate (Chem. Abstr., 1959, 3185d) with excess sodium cyanide in dimethylformamide there is obtained, in a yield of 90% of theory, ethyl 5-cyanomethylbenzo[b]furan-2-carboxylate (m.p. 74°-76° C. after recrystallisation from ethyl acetate) which is hydrogenated in the presence of platinum oxide to give ethyl 5-(2-aminoethyl)-benzo[b]furan-2-carboxylate. From an ethanolic solution thereof, with an ethereal solution of hydrogen chloride there can be precipitated out the hydrochloride; m.p. 188°-190° C.; yield 64% of theory.

EXAMPLE 2.

In a manner analogous to that described in Example 1, from ethyl 5-(2-aminoethyl)-benzo[b]furan-2-carboxylate hydrochloride and the appropriate sulphonic acid derivatives, there are obtained the following compounds:

| | designation | yield | m.p. °C. (solvent) |
| --- | --- | --- | --- |
| (a) | ethyl 5-(2-benzenesulphonamidoethyl)-benzo[b]furan-2-carboxylate from benzenesulphochloride | 41 | 84–86 (ethyl acetate) |
| (b) | ethyl 5-[2-(4-methylbenzenesulphonamido)-ethyl]-benzo[b]furan-2-carboxylate from p-toluenesulphonic acid anhydride | 49 | 101–103 (ethyl acetate) |
| (c) | ethyl 5-[2-(3-methylbenzenesulphonamido)-ethyl]benzo[b]furan-2-carboxylate from 3-methylbenzenesulphochloride | 57 | 86–88 (dichloromethane) |
| (d) | ethyl 5-[2-(4-methoxybenzenesulphonamido)-ethyl]-benzo[b]furan-2-carboxylate from 4-methoxybenzenesulphochloride | 52 | 91–93 (dichloromethane) |
| (e) | ethyl 5-[2-(4-bromobenzenesulphonamido)-ethyl]-benzo[b]furan-2-carboxylate from 4-bromobenzenesulphochloride | 51 | 132–135 (ethyl acetate) |

EXAMPLE 3.

Ethyl 5-[2-(4-chlorobenzenesulphonamido)-ethyl]-benzo[b]thiophene-2-carboxylate.

In a manner analogous to that described in Example 1, the title compound is obtained from 4-chlorobenzenesulphochloride and ethyl 5-(2-aminoethyl)-benzo[b]-thiophene-2-carboxylate.

EXAMPLE 4.

Ethyl 5-[2-(4-chlorobenzenesulphonamido)-ethyl]-3-methyl-benzo[b]furan-2-carboxylate.

In a manner analogous to that described in Example 1, the title compound is obtained from 4-chlorobenzenesulphochloride and ethyl 5-(2-aminoethyl)-3-methylbenzo-[b]furan-2-carboxylate.

EXAMPLE 5.

Ethyl 5-(4-chlorobenzenesulphonamido)-methyl)-benzo[b]-furan-2-carboxylate.

In a manner analogous to that described in Example 1, the title compound is obtained from 4-chlorobenzenesulphochloride and ethyl 5-aminomethylbenzo[b]furan-2-carboxylate.

EXAMPLE 6.

Ethyl 6-[2-(4-chlorobenzenesulphonamido)-ethyl]-benzo-[b]furan-2-carboxylate.

In a manner analogous to that described in Example 1, the title compound is obtained from 4-chlorobenzenesulphochloride and ethyl 6-(2-aminoethyl)-benzo[b]-furan-2-carboxylate.

EXAMPLE 7.

Ethyl 4-[2-(4-chlorobenzenesulphonamido)-ethyl]-benzo-[b]-furan-2-carboxylate.

In a manner analogous to that described in Example 1, the title compound is obtained from 4-chlorobenzenesulphochloride and ethyl 4-(2-aminoethyl)-benzo[b]-furan-2-carboxylate.

EXAMPLE 8.

Ethyl 5-[2-(4-chlorobenzenesulphonamido)-ethyl]-2,3-dihydrobenzo[b]furan-2-carboxylate.

In a manner analogous to that described in Example 1, the title compound is obtained from 4-chlorobenzenesulphochloride and ethyl 5-(2-aminoethyl)-2,3-dihydrobenzo[b]furan-2-carboxylate.

EXAMPLE 9.

Ethyl 5-[2-(4-chlorobenzenesulphonamido)-ethyl]-indole-2-carboxylate.

In a manner analogous to that described in Example 1, the title compound is obtained from 4-chlorobenzenesulphochloride and ethyl 5-(2-aminoethyl)-indole-2-carboxylate; yield 34% of theory; m.p. 193°–195° C., after recrystallisation from ethanol.

EXAMPLE 10.

Ethyl 5-[2-(4-chlorobenzenesulphonamido)-ethyl]-N-hydroxyindole-2-carboxylate.

In a manner analogous to that described in Example 1, the title compound is obtained from 4-chlorobenzenesulphochloride and ethyl 5-(2-aminoethyl)-N-hydroxyindole-2-carboxylate.

EXAMPLE 10a.

Ethyl 5-[2-(4-tert.-butylbenzenesulphonamido)-ethyl]-benzo[b]furan-2-carboxylate.

In a manner analogous to that described in Example 1, the title compound is obtained from 4-tert.-butylbenzenesulphochloride and ethyl 5-(2-aminoethyl)-benzo[b]furan-2-carboxylate.

EXAMPLE 11.

5-[2-(4-Chlorobenzenesulphonamido)-ethyl]-benzo[b]-furan-2-carboxylic acid.

A mixture of 5.0 g. (12.2 mMole) of the compound of Example 1, 25 ml. ethanol and 25 ml. 2N aqueous sodium hydroxide solution is stirred for 1 hour at 50° C., then evaporated, washed with ethyl acetate, the aqueous phase acidified, filtered and the precipitate dried in a vacuum. There are obtained 4.3 g. of the title compound (93% of theory); m.p. 193°–195° C.

EXAMPLE 12.

The following compounds are obtained in a manner analogous to that described in Example 12:

| | designation | yield % | m.p. °C. (solvent) |
|---|---|---|---|
| (a) | 5-(2-benzenesulphonamido)-ethylbenzo[b]furan-2-carboxylic acid from the compound of Example 2a | 92 | 222–225 (water) |
| (b) | 5-[2-(4-methylbenzenesulphonamido)-ethyl]-benzo[b]furan-2-carboxylic acid from the compound of Example 2b | 95 | 209–211 (water) |
| (c) | 5-[2-(3-methylbenzenesulphonamido)-ethyl]-benzo[b]furan-2-carboxylic acid from the compound of Example 2c | 94 | 212–214 (water) |
| (d) | 5-[2-(4-methoxybenzenesulphonamido)-ethyl]-benzo[b]furan-2-carboxylic acid from the compound of Example 2d | 85 | 194–196 (water) |
| (e) | 5-[2-(4-bromobenzenesulphonamido)-ethyl]-benzo[b]furan-2-carboxylic acid from the compound of Example 2e | 93 | 198–200 (water) |
| (f) | 5-[2-(4-chlorobenzenesulphonamido)-ethyl]-benzo[b]thiophene-2-carboxylic acid from the compound of Example 3 | | |
| (g) | 5-[2-(4-chlorobenzenesulphonamido)-ethyl]-3-methylbenzo[b]furan-2-carboxylic acid from the compound of Example 4 | 78 | 201–202 (ethyl acetate) |
| (h) | 5-(4-chlorobenzenesulphonamidomethyl)-benzo[b]furan-2-carboxylic acid from the compound of Example 5 | 51 | 234–238 (ethyl acetate) |
| (i) | 6-[2-(4-chlorobenzenesulphonamido)-ethyl]-benzo[b]furan-2-carboxylic acid from the compound of Example 6 | | |
| (j) | 4-[2-(4-chlorobenzenesulphonamido)-ethyl]-benzo[b]furan-2-carboxylic acid from the compound of Example 7 | | |
| (k) | 5-[2-(4-chlorobenzenesulphonamido)-ethyl]-2,3-dihydro- | | |

-continued

| | designation | yield % | m.p. °C. (solvent) |
|---|---|---|---|
| | benzo[b]furan-2-carboxylic acid from the compound of Example 8 | | |
| (l) | 5-[2-(4-chlorobenzenesulphonamido)-ethyl]indole-2-carboxylic acid from the compound of Example 9 | 72 | 236-237 (glacial acetic acid) |
| (m) | 5-[2-(4-chlorobenzenesulphonamido)-ethyl]-N-hydroxyindole-2-carboxylic acid from the compound of Example 10 | | |
| (n) | 5-[2-(4-tert.-butylbenzenesulphonamido)-ethyl]-benzo[b]furan-2-carboxylic acid from the compound of Example 10a | 80 | 193-196 (diethyl ether) |

EXAMPLE 13.

5-(2-Benzenesulphonamidoethyl)-2,3-dihydrobenzo[b]furan-2-carboxylic acid.

A mixture of 1.2 g. of the compound of Example 2a, 50 ml. ethanol and 0.5 g. palladium-charcoal is heated to 100° C. for 3 days under 280 bar hydrogen pressure. The reaction mixture is mixed with dilute aqueous sodium hydroxide solution, heated to 50° C. for 2 hours, filtered, acidified, filtered and the precipitate purified by chromatography. There are obtained 300 mg. (25% of theory) of the title compound; m.p. 132°-133° C., recrystallised from diethyl ether.

EXAMPLE 14.

Ethyl 5-[2-(4-chlorobenzenesulphonamido)-ethyl]-indole-2-carboxylate.

The compound of Example 9 can also be obtained in the following way:

(a) 4-[2-(4-Chlorobenzenesulphonamido)-ethyl]-nitrobenzene.

To a mixture of 9.0 g. (44 mMole) 4-nitrophenethylamine hydrochloride (Chem. Bu., 45, 2431/1921), 100 ml. dichloromethane and 13.5 g. triethylamine is added dropwise, while cooling with ice, a solution of 9.8 g. (44 mMole) 4-chlorobenzenesulphochloride in 50 ml. dichloromethane. The reaction mixture is further stirred for 1 hour, poured on to ice, extracted with dichloromethane, dried and evaporated. There are obtained 14.0 g. of the title compound (89% of theory); m.p. 151°-152° C., recrystallised from ethanol.

(b) 4-[2-(4-chlorobenzenesulphonamido)-ethyl]-aniline hydrochloride.

11.5 g. (34 mMole) of the nitro compound obtained above in a) are hydrogenated in 1 liter of methanol in the presence of 0.5 g. sulphided platinum catalyst. After the take up of the calculated amount of hydrogen, the reaction mixture is filtered and the filtrate mixed with an ethereal solution of hydrogen chloride. There are obtained 10.5 g. of the title compound (quantitative); m.p. 228°-230° C.

(c) Pyruvic acid-4-[2-(4-chlorosulphonamido)-ethyl]-phenylhydrazone.

A mixture of 8.9 g. (26 mMole) of the hydrochloride obtained above in b), 300 ml. water and 14 ml. concentrated hydrochloric acid is mixed at ambient temperature with a solution of 1.8 g. sodium nitrate in 20 ml. water. To a mixture of 3.9 g. (26 mMole) ethyl 2-methylacetoacetate and 100 g. ice water is simultaneously added dropwise the above diazonium salt solution, as well as a solution of 14 g. potassium hydroxide in 40 ml. water. The reaction mixture is further stirred for 15 minutes, acidified with hydrochloric acid, extracted with diethyl ether, dried and evaporated. There are obtained 13.0 g. (91% of theory) of the title compound in the form of a red oil which is further reacted in the crude form.

(d) Ethyl 5-[2-(4-chlorobenzenesulphonemido)-ethyl]-indole-2-carboxylate.

A mixture of 1.0 g. (2.4 mMole) of the oil obtained in (c), 9 ml. glacial acetic acid and 1 ml. concentrated sulphuric acid is heated to the boil for 5 minutes. The reaction mixture is poured on to ice, extracted with ethyl acetate, washed neutral, dried and evaporated. After recrystallisation from ethanol, there are obtained 300 mg. (31% of theory) of the title compound; m.p. 192°-195° C.

It will be understood that the specification and examples are illustrative but not limitative of the present invention and that other embodiments within the spirit and scope of the invention will suggest themselves to those skilled in the art.

PROTOCOL OF EXPERIMENT

1. TX Antagonistic Effect of Human Erythrocytes

Method

The thrombocyte aggregation is investigated by the method of Born and Cross (J. Physiol. 168, 178 (1963) in platelet-rich plasma of healthy blood donors. To inhibit clotting, the blood is mixed with 3.2% citrate in a ratio by volume of 1:9.

To induce thrombocyte aggregation, U 46619 (Upjohn & Co., Kalamazoo, U.S.A.), which is a stable analog of the prostaglandin endoperoxide $PHG_2$, is used. U 46619 was characterized as a selective thromboxane mimetic (Coleman et al., Brit. J. Pharmacol. 68, 127 P., 1980).

The aggregation test is carried out in a 4-channel aggregometer (Profiler® of the Bio/Data Co., U.S.A.). The course of the aggregation is followed over a period of 5 minutes. At the end of the test, the degree of aggregation attained is printed out. These values, which are obtained in the presence of different concentrations of the substance to be tested, are used for the determination of the $EC_{50}$ for the TX antagonistic effect. The effectiveness varies inversely with the $EC_{50}$ value.

2. Preventing the U 46619-Induced Pulmonary Embolism

Method

Male NMRI mice, with a body weight of 25 g. are used. The test substance is suspended in 1% methylcellulose and administered to the experimental animals with the help of a stomach tube. The provocation test consists of injecting the lethal dose (800-1000 μg/kg) of the thromboxane mimetic (U 46619 of the Upjohn Co.) rapidly into the tail vein. The duration of the specific antagonistic effect is tested by pretreating the animals with 25 mg or 1 mg/kg of the different test substances and injecting U 46619 after 4 hours. The survival rate indicates how many of the animals used have survived the injection of the thromboxane mimetic. The results are given in the Table below

| Substance Example | Survival Rate of Mouse 25 mg/kg, 4 h | Survival Rate of Mouse 1 mg/kg, 4 h | Human Erythrocytes IC50 ($\mu$M) |
|---|---|---|---|
| 11 | 10/10 | 4/5 | 0.75 |
| 12 e | 5/5 | | 2.7 |
| 12 b | 4/5 | | 1.6 |
| 12 g | 5/5 | | 1.7 |
| 13 | 5/5 | | 1.2 |
| 12 l | | 2/5 | 1.4 |
| Comparison Compound | 2/2 | | 1.85 |

Comparison Compound: BM 13.177 = 4-[2-(benzenesulfonylamino)-ethyl]-7-phenoxyacetic acid from U.S. Pat. No. 4,258,058.

What is claimed:

1. A sulphonamide of the formula

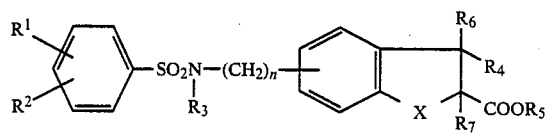

wherein $R_1$ and $R_2$, which can be the same or different, are hydrogen, halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, trifluoromethyl, hydroxyl, or cyano, $R_3$ and $R_8$, which can be the same or different, are hydrogen, $C_1$-$C_6$-alkyl, benzyl, or $C_1$-$C_6$-alkanoyl, $R_4$ and $R_5$, which can be the same or different, are hydrogen or [$C_1C_6$-alkyl] $C_1$-$C_6$-alkyl, $R_6$ and $R_7$ are both hydrogen or together form a valency bond, X is oxygen or =$NR_8$ and n is a whole number from 1 to 4, a physiologically acceptable salt thereof with an inorganic or organic base and, when the compound comprises an asymmetric carbon, a racemic mixture or optically active form thereof.

2. The sulphonamide of claim 1 wherein, when $R_1$, $R_2$, $R_3$, $R_4$, $R_5$ or $R_8$ are alkyl, alkoxy, alkylthio, alkylsulphinyl, alkylsulphonyl or alkanoyl, each alkyl moiety thereof is selected from the group consisting of methyl, ethyl, propyl, isopropyl, butyl, sec-butyl, tert.-butyl, pentyl or hexyl.

3. The sulphonamide of claim 1, wherein $R_1$, $R_3$ and $R_8$ are hydrogen, $R_2$ is hydrogen, bromine, chlorine, methyl or methoxy, $R_4$ is hydrogen or methyl, $R_5$ is hydrogen or ethyl, $R_6$ and $R_7$ together form a valency bond, X is oxygen or =$NR_8$, n is 1 or 2, and the sulphonamido is in the 5-position of the heterocyclic moiety.

4. The sulphonamide of claim 1 consisting of 5-[2-(4-chlorobenzenesulphonamido)-ethyl]-benzo[b]-furan-2-carboxylic acid.

5. The sulphonamide of claim 1 consisting of 5-[2-(4-methylbenzenesulphonamido)-ethyl]-benzo[b]furan-2-carboxylic acid.

6. The sulphonamide of claim 1 consisting of 5-[2-(4-bromobenzenesulphonamido)-ethyl]-benzo[b]-furan-2-carboxylic acid.

7. The sulphonamide of claim 1 consisting of 5-[2-(4-chlorobenzenesulphonamido)-ethyl]-3-methylbenzo-[b]-furan-2-carboxylic acid.

8. The sulphonamide of claim 1 consisting of 5-[2-(4-chlorobenzenesulphonamido)-ethyl]indole-2-carboxylic acid.

9. The sulphonamide of claim 1 consisting of 5-(2-benzenesulphonamidoethyl)-2,3-dihydrobenzo[b]-furan-2-carboxylic acid.

10. A pharmaceutical composition comprising a pharmaceutically effective amount of at least one of the compounds of claim 1, in a pharmaceutically acceptable carrier.

11. A composition according to claim 10 in which the compound is selected from the group consisting of
5-[2-(4-chlorobenzenesulphonamido)-ethyl]-benzo[b]-furan-2-carboxylic acid,
5-[2-(4-methylbenzenesulphonamido)-ethyl]-benzo[b]-furan-2-carboxylic acid,
5-[2-(4-bromobenzenesulphonamido)-ethyl]-benzo[b]-furan-2-carboxylic acid,
5-[2-(4-chlorobenzenesulphonamido)-ethyl]-3-methyl-benzo[b]furan-2-carboxylic acid,
5-[2-(4-chlorobenzenesulphonamido)-ethyl]-indole-2-carboxylic acid, and
5-(2-benzenesulphonamidoethyl)-2,3-dihydrobenzo[b]-furan-2-carboxylic acid.

12. A method for the treatment of peripheral arterial occlusive diseases which comprises administering to a patient in need of such treatment amount of a compound of the formula

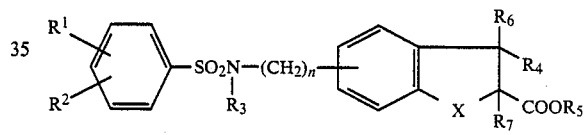

wherein $R_1$ and $R_2$, which can be the same or different, are hydrogen, halogen, $C_1$-$C_6$-alkyl, $C_1$-$C_6$-alkoxy, $C_1$-$C_6$-alkylthio, $C_1$-$C_6$-alkylsulphinyl, $C_1$-$C_6$-alkylsulphonyl, trifluoromethyl, hydroxyl, or cyano, $R_3$ and $R_8$, which can be the same or different, are hydrogen, $C_1$-$C_6$-alkyl, benzyl, or $C_1$-$C_6$-alkanoyl, $R_4$ and $R_5$, which can be the same or different, are hydrogen or $C_1$-$C_6$-alkyl, $R_6$ and $R_7$ are both hydrogen or together form a valency bond, X is oxygen or =$NR_8$, and n is a whole number from 1 to 4, a physiologically acceptable salt thereof with an inorganic or organic base and, when the compound comprises an asymmetric carbon, a racemic mixture or optically active form thereof.

13. The method of claim 12 comprising administering to said patient a daily dose of the compound of from 0.1 to 50 mg/kg body weight.

14. The method of claim 13 comprising administering to said patient a daily dose of the compound of from 0.5 to 40 mg/kg body weight.

15. The method of claim 14 comprising administering to said patient a daily dose of the compound of from 1.0 to 20 mg/kg body weight.

16. The method according to claim 12 in which the compound is

5-[2-(4-chlorobenzenesulphonamido)-ethyl]-benzo[b]-furan-2-carboxylic acid.

17. The method according to claim 12 in which the compound is

5-[2-(4-methylbenzenesulphonamido)-ethyl]-benzo[b]-furan-2-carboxylic acid;

18. The method according to claim 12 in which the compound is

5-[2-(4-bromobenzenesulphonamido)-ethyl]-benzo[b]-furan-2-carboxylic acid.

19. The method according to claim 12 in which the compound is

5-[2-(4-chlorobenzenesulphonamido)-ethyl]-3-methyl-benzo[b]furan-2-carboxylic acid.

20. The method according to claim 12 in which the compound is

5-[2-(4-chlorobenzenesulphonamido)-ethyl]-indole-2-carboxylic acid.

21. The method according to claim 12 in which the compound is 5-(2-benzenesulphonamidoethyl)-2,3-dihydrobenzo[b]-furan-2-carboxylic acid.

* * * * *